(12) United States Patent
Macdonald et al.

(10) Patent No.: US 11,918,509 B1
(45) Date of Patent: Mar. 5, 2024

(54) LOVE NEST (71) Applicants: Kathryn L. Macdonald, Bedford, TX (US); Ryan Macdonald, Bedford, TX (US)

(72) Inventors: Kathryn L. Macdonald, Bedford, TX (US); Ryan Macdonald, Bedford, TX (US)

( * ) Notice: Subject to any disclaimer, the term of this patent is extended or adjusted under 35 U.S.C. 154(b) by 292 days.

(21) Appl. No.: 17/001,708

(22) Filed: Aug. 25, 2020

Related U.S. Application Data (63) Continuation-in-part of application No. 16/740,450, filed on Jan. 12, 2020, now abandoned.

(51) Int. Cl.
A61F 6/08 (2006.01)
A61F 6/14 (2006.01)

(52) U.S. Cl.
CPC ..................... A61F 6/08 (2013.01)

(58) Field of Classification Search
CPC ..... A61F 6/08; A61F 6/06; A61F 6/14; A61B 17/425; A61D 19/02; A61D 19/021; A61D 19/022; A61D 19/024
USPC .................................................. 600/33–35
See application file for complete search history.

(56) References Cited

U.S. PATENT DOCUMENTS

| | | | | | |
|---|---|---|---|---|---|
| 2,764,975 | A | * | 10/1956 | Greenberg | A61B 17/43 600/35 |
| 2,855,932 | A | * | 10/1958 | Stubbs | A61B 17/43 600/35 |
| 4,770,167 | A | * | 9/1988 | Kaali | A61F 6/08 128/833 |
| 5,857,959 | A | * | 1/1999 | La Vean | A61F 6/08 600/33 |
| 2007/0256691 | A1 | * | 11/2007 | Ogram | A61B 17/43 128/830 |
| 2013/0267769 | A1 | * | 10/2013 | La Vean | A61F 6/08 600/33 |
| 2019/0282350 | A1 | * | 9/2019 | Conti | A61F 6/12 |
| 2020/0015854 | A1 | * | 1/2020 | Jacoby | A61B 17/425 |
| 2021/0267640 | A1 | * | 9/2021 | Stal | A61B 17/43 |
| 2023/0048673 | A1 | * | 2/2023 | Sina Raja | A61B 90/03 |

FOREIGN PATENT DOCUMENTS

| | | | | |
|---|---|---|---|---|
| GB | 2579538 A | * | 7/2000 | |
| GB | 2579538 A | * | 7/2020 | ........... A61B 17/425 |

OTHER PUBLICATIONS

Lavean, Cervical cap with hanging loop for removal, WO 99/36011, Jul. 22, 1999.*

* cited by examiner

*Primary Examiner* — Camtu T Nguyen
(74) *Attorney, Agent, or Firm* — Law Office of Jeff Williams PLLC; J. Oliver Williams (57) ABSTRACT

A device for enhancing the chance of conception is disclosed.

1 Claim, 7 Drawing Sheets

LOVE NEST

BACKGROUND OF THE INVENTION

A. Technical Field

The present invention generally relates to a vaginal device. More specifically, the present invention relates to a device that increases the chance of conception by capturing sperms from a vaginal wall and assisting the migration of the sperms into cervix and uterus.

B. Description of Related Art

The conception of a child is a simple process for some women, while being a frustrating experience for others. Over the course of a woman's reproductive years, an average of four hundred eggs are released. An egg attaining maturity during the middle of the menstrual cycle, is released into an opening of the fallopian tube. The release of the egg into the fallopian tube is called ovulation. The egg lives for 24 hours after the ovulation process begins, and must be fertilized within the specified time. If the egg encounters a healthy sperm on its way to the uterus, the process of conception begins. However, if the fertilization of the egg does not occur before the egg reaches the uterus, the egg is either dissolved or absorbed back into the body.

Sperm can live in a woman's reproductive tract for as long as five days in few individuals. The survival of the sperm in the body and the reaching of the sperm in the area is necessary for the occurrence of conception. Gravity is one of the factor responsible for the viable sperm reaching the desired area for conception, which is dependent on the body position of the individual. After the intercourse, the vagina is inseminated with 180 to 400 million sperms. These microscopic (50 millionths of an inch) spermatozoa, are conditioned to move forward, swimming by moving their tails and propelling the 5 micron heads everywhere within the vagina. Some of the sperms that move toward the closed end of the vagina, encounter the opening to the uterus, the cervix, and swim into the uterus to fertilize the ovum. When the egg attached to the wall of the uterus contacts with the spermatozoa, the egg is fertilized. However, some of the sperms gets dispersed throughout the vaginal wall, and do not reach to an opening of the cervix. The sperms dispersed in the vaginal wall are wasted, as they cannot migrate towards the cervix, thereby decreasing the chance of conception.

In light of the foregoing, there is a need for a device that could collect the sperms dispersed in the walls of the vagina after intercourse. Further, there is need for the device in assisting the collected sperm to migrate towards the cervix/uterus for enhancing the chances of conception.

SUMMARY OF THE INVENTION

The present invention relates to a device that increases the chance of conception by capturing and assisting sperms into cervix and uterus. The device is cost effective and easy to use. The device resolves the problem associated with the wastage of sperm dispersed throughout the vaginal wall after intercourse, by collecting any errant sperm in the vagina, and positioning them at the cervical opening. This improves the probability of the movement of the viable sperm into the uterus, resulting in fertilization of an egg The device of the present invention increases the chance of conception of a user, by collecting the sperm dispersed in the vaginal wall after intercourse, and further assisting the collected sperm towards the cervix and the uterus. The device is inserted inside a vaginal canal close as to a cervix after intercourse. In an embodiment, the user gently pushes the device up into the vagina, until an interior surface of the device with a cup shaped structure is resting upon an exterior surface of the cervix. In an embodiment, the device comprises a cup or a cup shaped structure, and a valve. In one embodiment, the cup is a textured flexible cup. In some embodiments, the cup is made of material, but not limited to plastic. In one embodiment, an outer surface of the cup shaped structure includes a soft raised texture configured to hold the device in particular place or position. In one embodiment, the valve of the device is configured to prevent the sperm from drifting downwards. The valve is a one-way valve, which allows sperm in but not out. In some embodiments, the valve is a diode type valve. The cup and valve are configured to assist the sperm in migrating back into the cervix/uterus.

In an embodiment, the cup shaped structure is injection molded using a medical grade plastic material. The plastic material for example is but not limited to polypropylene.

A device being configured to capture sperm into a cervix and an uterus, may include a cylinder shaped structure having a central passageway and configured to prevent sperm from attaching to a vaginal wall having a first section having a substantially constant diameter and a second section having a truncated continual decreasing diameter configured to prevent the sperm from attaching to the vaginal wall;

A device may be configured to capture sperm into a cervix and an uterus wherein the cylinder shaped structure may include a radial lip extending inwards.

A device may be configured to capture sperm into a cervix and an uterus wherein the cylinder shaped structure may include a first outward extending lip positioned on a first end of the cylinder shaped structure.

4) A device being configured to capture sperm into a cervix and an uterus wherein the cylinder shaped structure may include a second outward extending lip positioned on a second end of the cylinder shaped structure.

5) A device being configured to capture sperm into a cervix and an uterus wherein the cylinder shaped structure may include outward extending projections mounted on a outer surface of the cylinder shaped structure.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1A:
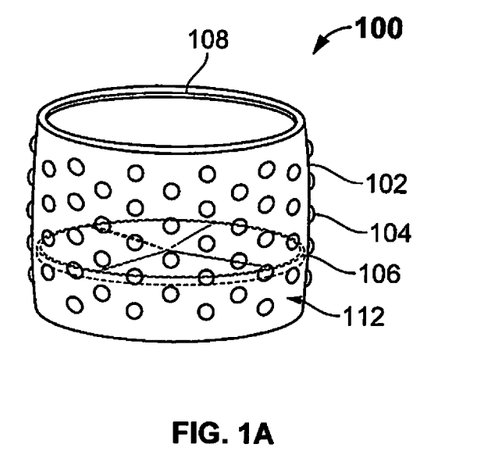
FIG. 1A is a front perspective view of a device, according to an embodiment of the present invention.
Figure 1B:
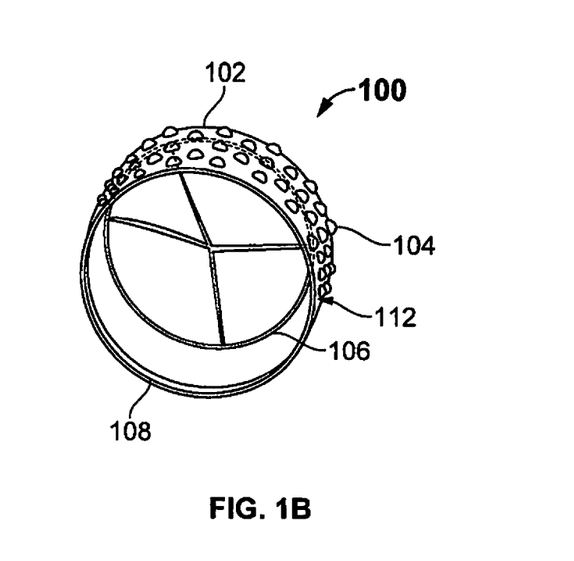
FIG. 1B is a side perspective view of the device, according to an embodiment of the present invention.

FIG. 1A and FIG. 1B illustrate a front perspective and side perspective view of a device 100, according to an embodiment of the present invention. The device 100 is configured to capture sperm into a cervix and uterus. The device 100 is inserted inside a vaginal canal as close to the cervix. In an embodiment, the device 100 is a vaginal device used after intercourse. In one embodiment, the device 100 comprises a cup or cup shaped structure 102, and a valve 104. In an embodiment, the cup shaped structure 102 is soft and flexible configured to capture sperm present within a vaginal wall. In one embodiment, the cup 102 is a textured flexible cup. In some embodiments, the cup 102 is made of material, but not limited to plastic. In one embodiment, the cup shaped structure 102 could be a cylindrical cup shaped structure.

In one embodiment, an outer surface 112 of the cup shaped structure 102 includes a soft raised texture 106 configured to hold the device 100 in particular place or position. In one embodiment, the valve 104 is disposed on the top portion of the device 100. In one embodiment, the valve 104 of the device 100 is configured to prevent the sperm from drifting downwards. The valve 104 is a one-way valve, which allows sperm in, but not out. In some embodiments, the valve 104 is a diode type valve. In another embodiment, the cup shaped structure 102 and the valve 104 are configured to assist the sperm in migrating back into the cervix/uterus. Further, referring to FIG. 1A and FIG. 1B, the device 100 comprises a band member 108 on the top border portion of the device 100. The band member 108 further helps in positioning the device 100 in the vaginal canal as close to the cervix as possible to capture the semen.

Figure 2:
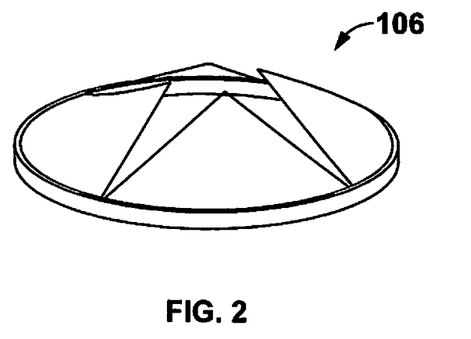
FIG. 2 is a perspective view of opened valve of the device, according to an embodiment of the present invention.
Figure 3:
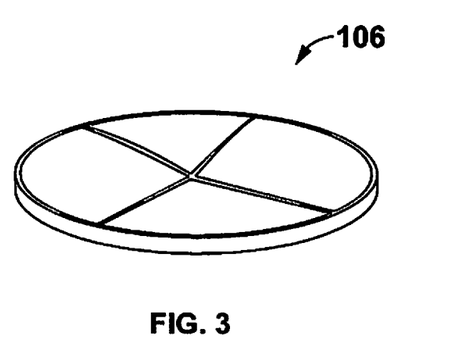
FIG. 3 is a perspective view of closed valve of the device, according to an embodiment of the present invention.

Referring to FIG. 2 and FIG. 3, a perspective view of the valve 104 in open and closed position is illustrated. The valve 104 is configured to be placed nearer to the opening end of the vaginal canal. The valve 104 of the device 100 is configured to prevent the sperm from drifting downwards.

The valve 104 is a one-way valve, which allows sperm in, but not out. In some embodiments, the valve 104 is a diode type valve. In another embodiment, the cup shaped structure 102 and the valve 104 are configured to assist the sperm in migrating back into the cervix/uterus. In some embodiments, the valve 104 could be an integral part of the cup shaped structure 102, when the device 100 is in use.

In an embodiment, the cup shaped structure 102 of the device 100 is injection molded using a medical grade plastic material. The plastic material for example is but not limited to polypropylene. The plastic material is selected from any medical grade plastic material that serves the objective of the invention. In another embodiment, the cup shaped structure 102 is soft, flexible and its outer surface 112 is configured with multiple soft raised structures made of similar material that hold the device 100 in particular place or position.

In an embodiment, the band member 108 is positioned above the cup shaped structure 102. The upper end of the cup shaped structure 102 is attached or matted with the band member 108. The band member 108 remains integral to the cup shaped structure 102, when the device 100 is in use. In one embodiment, the band member 108 is molded using medical grade rubber material. The rubber material for example is but not limited to a medical grade silicone rubber. Both the band member 108, and the cup shaped structure 102 are flexible, making the insertion painless and easy, regardless of the vaginal size. The band member 108 is flexible, and expands to hold itself in place. The cup shaped structure 102, valve 104, soft raised or protruding texture 106, and band member 108 is supplied in almost any vibrant color, to enhance the recognition factor of the device 100 for improvement of market adaption.

The device 100 is sanitized and dried prior to packaging. The device 100 are stacked in groups of twelve, and then inserted in a sanitized point-of-sale carton. In another embodiment, after sanitization and prior to packaging, the interior surface of each of the cup shaped structures 102 is sprayed with a very thin film of potassium, magnesium, and fructose at a pH of 7 to 7.5. After spraying, the film is dried and then the product is grouped in stacks of 12. This coating increases the motility of the sperm by providing the correct pH environment, and feeding them sugar and electrolytes to enhance activity.

In one embodiment, the cup-shaped structure 102 and valve 104 of the device 100 scrapes off the sperm from an interior wall of the vagina as the device 100 is inserted into the vaginal canal after intercourse. Due to gravity, the collected sperm slide towards the center of the cup shaped structure 102, and further migrate towards the opening in the cervix. Further, the cup shape structure 102 also collects any errant sperm loose within the vagina. The device 100 is discarded after single use, as it is made of inexpensive medical grade materials by simple molding process. The medical grade, inert plastic does not affect the mobility or vigor of the sperm during wear or use of the device 100. In one embodiment, a portion of the cup shaped structure 102 towards the cervix is coated with a thin film of potassium, magnesium, and fructose at a pH of 7 to 7.5 to increase the motility of the sperm.

Figure 4A:
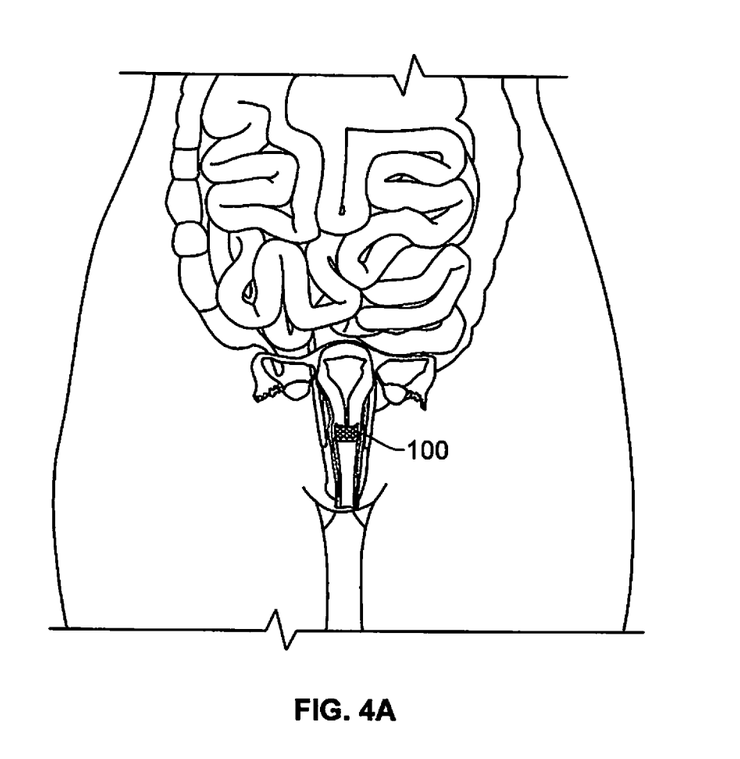
FIG. 4A is a front view of a vaginal canal illustrating the insertion of the device, according to an embodiment of the present invention.

FIG. 4A is a front view of the vaginal canal illustrating the insertion of the device, 100 according to an embodiment of the present invention. The device 100 helps in increasing the chance of conceiving a child. The device 100 is soft, flexible, and worn by a user immediately after an intercourse has occurred. In an embodiment, the user is a woman trying to conceive. The user has to insert the device 100 into the vaginal canal as close to the cervix for using the device 100. The device 100 is configured to capture any sperm falling from the cervix/uterus or that is left in the vaginal wall. It helps in keeping the sperm available, and in the vicinity for fertilization. The cup shaped structure 102 contains the sperm at the center, allowing the sperm to migrate back into the cervix/uterus area for enhancing the chances of fertilization. In an embodiment, the user could wear the device for 8 to 12 hours. The user could place, or insert the device 100 within the vagina without any medical procedures or help of any medical practitioners. The user, while wearing the device 100 could carry out normal household activities. The removal of the device 100 from the vagina is very easy.

Figure 4B:
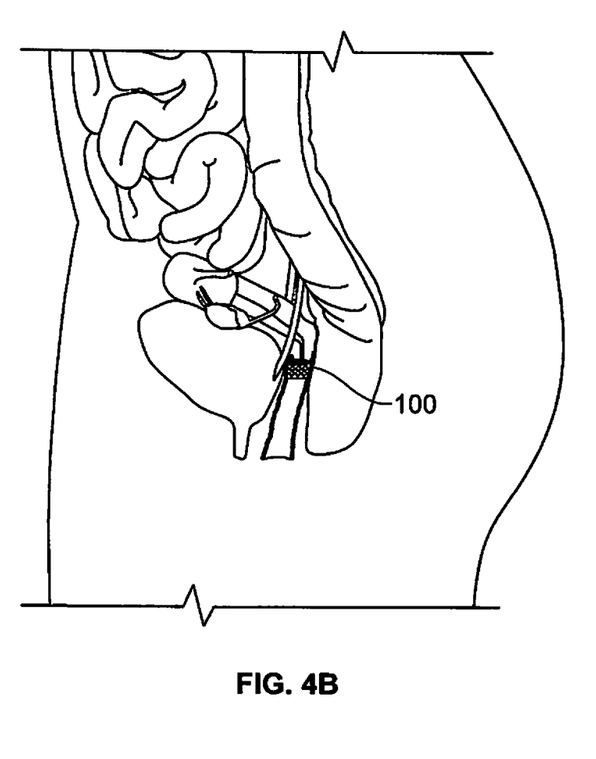
FIG. 4B is a side view of the vaginal canal illustrating the insertion of the device, according to an embodiment of the present invention.

FIG. 4B is a side view of the vaginal canal illustrating the insertion of the device 100, according to an embodiment of the present invention. In an embodiment, the user gently pushes the device 100 up into the vagina, until the interior surface of the cup shaped structure 108 is resting upon an exterior surface of the cervix. The rubber ring 104 on the cup shaped structure 102 gently 'wipes' the interior walls of the vagina, and captures the sperm within the cup shaped structure 102. The device 100 is disposed in an appropriate container. The inert components and the flexible construction allow easy insertion of the device 100 with no effect upon the spermatozoa, and dramatically improving the chance to get pregnant. The device improves the probability of the movement of the viable sperm into the uterus, resulting in fertilization of an egg In an embodiment, the cup shaped structure 102 is a supple malleable plastic cup suspended from a fastened and pliable band. The device 100 collects the sperm dispersed in the vaginal wall after intercourse, and thus assist the sperm to migrate to the cervix/the uterus increasing the chance to conceive. The user could easily insert and remove the device 100 without the help of the medical procedures or practitioners. The device 100 is cost effective and easily affordable by any section of the people.

Figure 5:
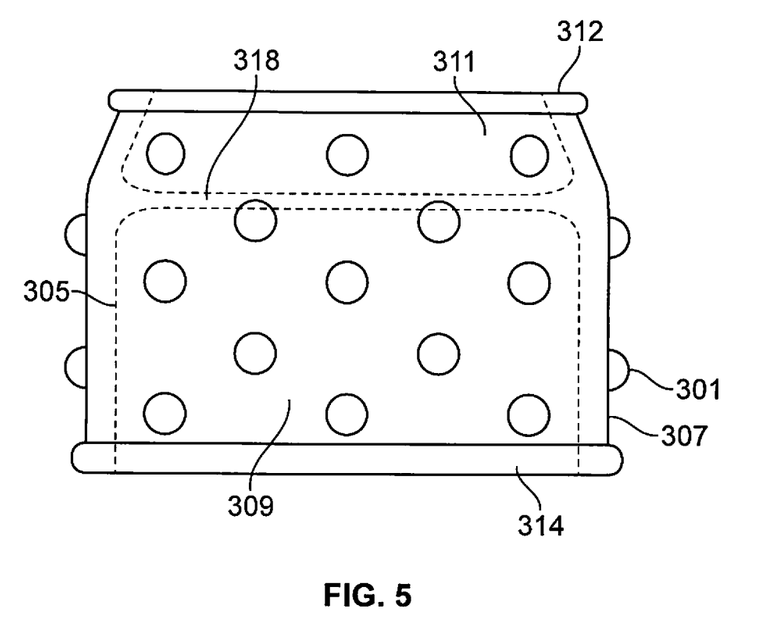
FIG. 5 illustrates a side view of the another vaginal device of the present invention.
Figure 6:
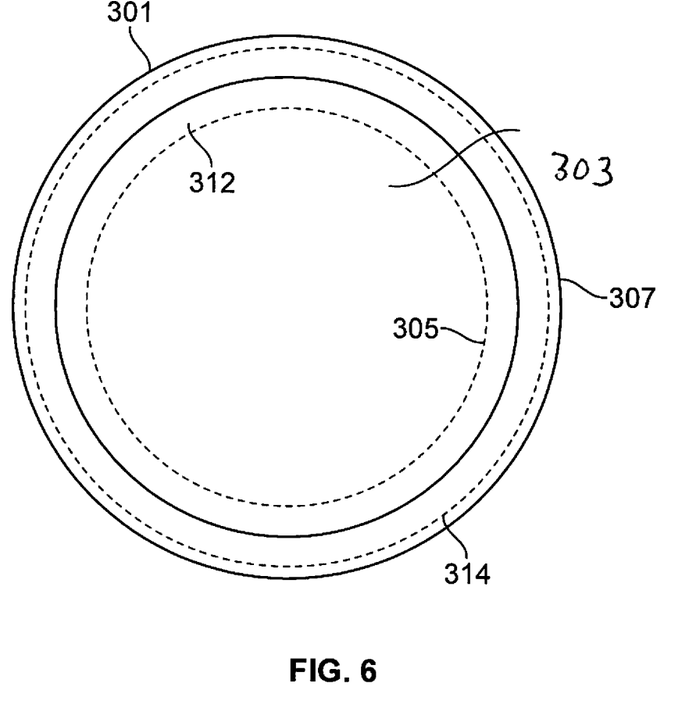
FIG. 6 illustrates a top view of the another vaginal device of the present invention.
Figure 7:
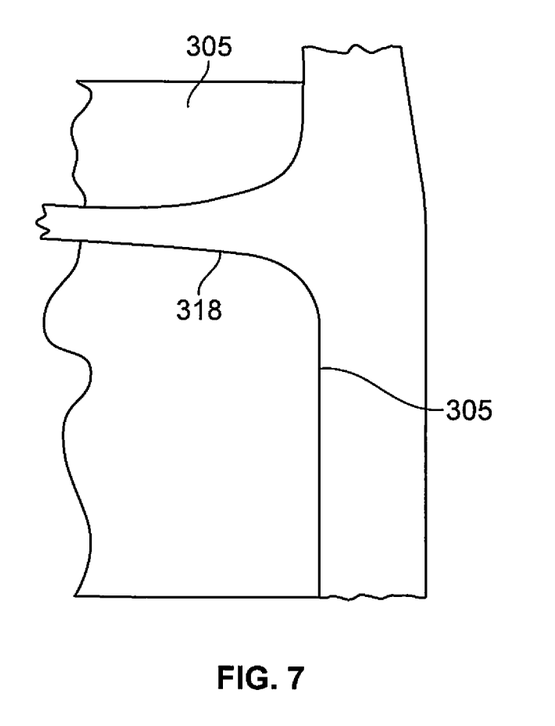
FIG. 7 illustrates a cutaway view of the another vaginal device of the present invention.

\FIGS. 5-7 illustrate another virginal device 300 of the present invention which may be a cylinder shaped structure 301 and having a central passageway 303 extending through the virginal device 300. The device 300 may be oval or other shaped device. The cylinder shaped structure 301 includes an interior surface 305 which may extend around the periphery of the central passageway 303 and an exterior surface 307 which may define the shape of the device 300 and which may be configured to provide a friction fit with the virginal wall. The cylinder shaped structure 301 may include a first section 309 and a second section 311, and the first section 309 may have a substantially constant diameter while the second section 311 may have a truncated continual decreasing diameter.

At each end of the central passageway 303 is an outward extending lip 312, 314 which presses against the virginal wall in order to provide an increased frictional fit with the vagina and the outward extending lip 312, 314 extends around the perimeter of the central passageway 303 and may be formed on the outer surface 307 additionally, a plurality of outward extending projections may be formed on the outer surface 307 in order to increase the frictional fit with the vagina. An inward extending internal radial lip 318 may extend around the interior surface 305 and may be positioned between the extend between the first section 309 and the second section 311.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

The invention claimed is:

1. A device being configured to enhance a chance of conception within an uterus, comprising:
  a cylinder shaped structure having a central passageway with an internal surface and being configured to prevent sperm from attaching to a vaginal wall, the cylinder shaped structure including a first section having a constant diameter and a second section having a truncated continual decreasing diameter;
  an internal radial lip located between the first section and the second section and extending circumferentially along the internal surface, the internal radial lip configured to prevent passage between the first section and the second section;
  a first external radial lip located at an opening of the first section; and
  a second external radial lip located at an opening of the second section.

* * * * *